United States Patent [19]

Freeman et al.

[11] Patent Number: 5,902,888
[45] Date of Patent: May 11, 1999

[54] SYNTHESIS OF 6α-FUNCTIONALIZED ESTRIOL HAPTENS AND PROTEIN CONJUGATES THEREOF

[75] Inventors: James V. Freeman, Granger; Gary M. Johnson, Elkhart, both of Ind.

[73] Assignee: Bayer Corporation, Elkhart, Ind.

[21] Appl. No.: 08/970,139

[22] Filed: Nov. 14, 1997

[51] Int. Cl.$^6$ ............................ C07D 301/27; C07J 41/00
[52] U.S. Cl. ............................................. 552/515; 540/106
[58] Field of Search ............................... 552/515; 540/106

[56] References Cited

FOREIGN PATENT DOCUMENTS 2330159  6/1973  Germany .

OTHER PUBLICATIONS

Hamacher et al, *Arzneim–Forsch./Drug Res.*, 33 (1), 347–352 (1983).
Frei et al, *J. Steroid Biochem.*, 32 (2), 251–257 (1989).
Nambara et al, *Chem. Pharm. Bull.*, 22 (5), 1167–1173 (1974).
Longwell et al, *Biol. Chem.*, 133 219–229 (1940).
Smith et al, *J. Org. Chem.*, 37 (25) 4000–4002 (1972).
Jeffcoate et al, *Steroids*, 19 (2) 181–188 (1972).
Dean et al, *Steroids*, 593–603 (1971).

*Primary Examiner*—Paula K. Hutzell
*Assistant Examiner*—Lin Sun-Hoffman
*Attorney, Agent, or Firm*—Jerome L. Jeffers

[57] ABSTRACT

Disclosed are 6α-derivatized estriol compounds which, when conjugated to a protein, are useful in the in vivo preparation of antibodies specific to estriol. When labeled with a detectable label, the estriol derivatives are useful as haptens in a competitive immunoassay for estriol which demonstrate superior sensitivity with respect to estriol specific antibodies.

5 Claims, 1 Drawing Sheet

SYNTHESIS OF 6α-FUNCTIONALIZED ESTRIOL HAPTENS AND PROTEIN CONJUGATES THEREOF

BACKGROUND OF THE INVENTION

Estrogenic hormones are of primary importance in the female reproductive cycle and also play a role in mammary cancers. Estradiol is a potent, naturally occurring form of estrogen which may be associated with certain breast cancers. Estriol, related to estradiol, but differs in the respect that estradiol is the most potent naturally occurring estrogen whereas, estriol is a metabolite of and is considerably less potent than estradiol. Estriol is usually the predominant estrogenic metabolite found in urine and may be related to fetal distress. Accordingly, the detection of estriol serum levels in pregnant women provides information on fetal status during pregnancy. The clinical significance of estrogenic hormones is discussed by K. S. McCarty et al in *Regulatory Mechanisms in Breast Cancer*, Chapter 9, Kluwer Academic Publishers, Boston, 1991.

The synthesis of 6α-substituted estradiol analogs is discussed by Hamacaher et al in *Arzneurn Forsch./Drug Res.*, 33 (1), 347–352 (1983), Frei et al in *J. Steroid Biochem.*, 32 (2), 251–57 (1989), Nambura et al in *Chem. Pharm. Bull.*, 22 (5), 1167–1173 (1974) and Jeffcoate et al in *Steroids*, 19 (2), 181–188 (1972).

The preparation of compounds 2 and 3 of scheme 1 herein is described by Dean et al in *Steroids*, 593–603 (1971), Longwell et al in *Biol. Chem.*, 133, 219–299 (1940) and Burows et al in *J. Org. Chem.*, 37, 4000 (1972).

SUMMARY OF THE INVENTION

Figure 1:
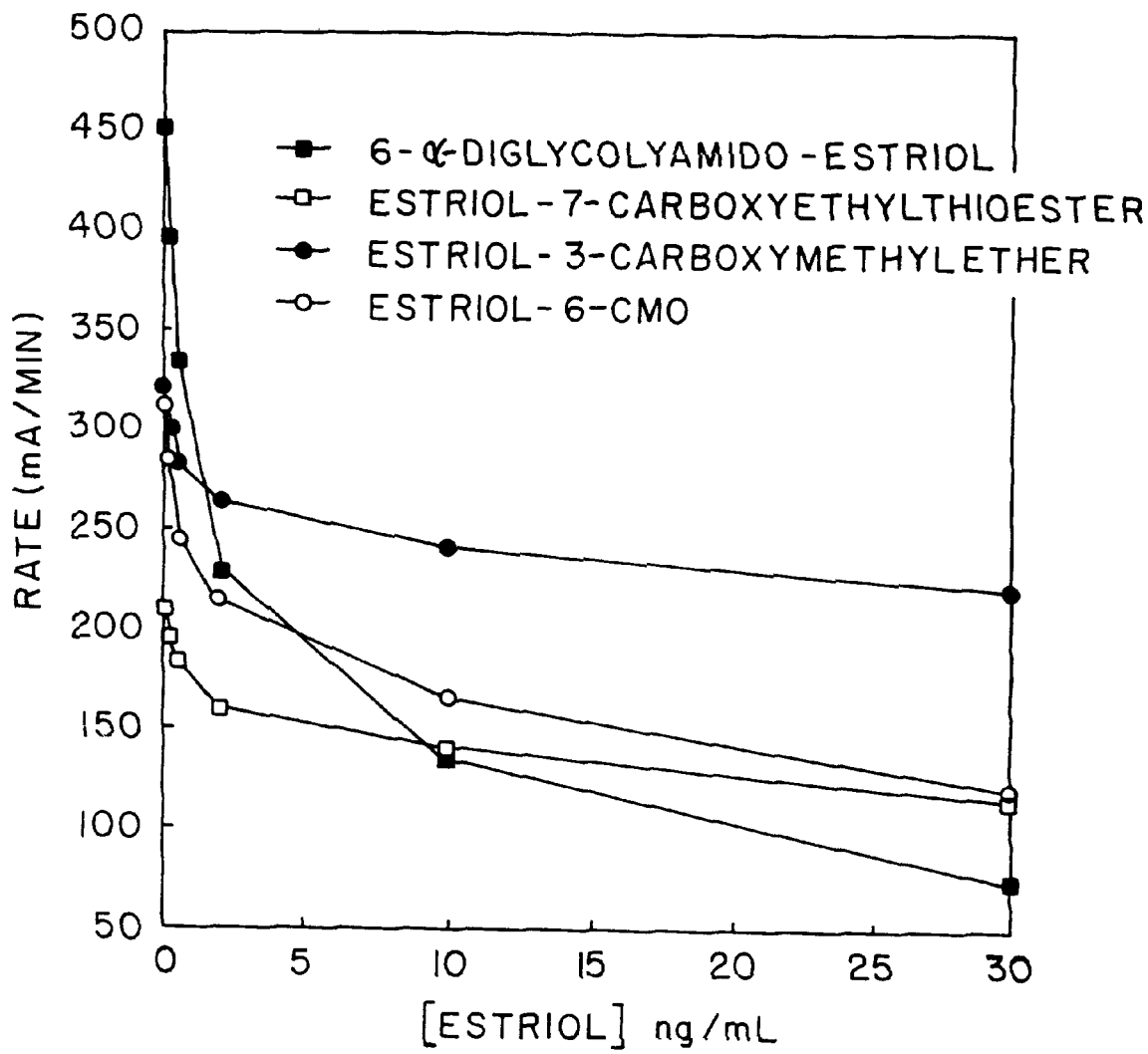
FIG. 1 represents a series of dose response curves for four different alkaline phosphatase (ALP) labeled estriol haptens.

The present invention involves the synthesis of stereochemically defined 6α-position derivatives of estriol suitable for coupling to proteins. Selection of the 6-position for derivatization and the α-stereochemistry increases the likelihood of obtaining reagents for estriol immunoassays which demonstrate minimal recognition of its metabolites.

DESCRIPTION OF THE INVENTION

The 6α-derivatized estriol compounds described herein can be used to synthesize hapten conjugates for use in heterogenous immunoassays as well as being useful for synthesizing immunogens for antibody development in animals such as rabbits, mice or goats. The hapten conjugates can be used together with polyclonal antibodies produced using the immunogen to detect free estriol in serum or plasma.

As described in more detail in the following examples, the 6α-estriol derivatives of the present invention can be prepared starting with 6-ketoestriol-3,16,17-triacetate which can be derived from known starting materials using standard techniques. The estriol triacetate is reacted with about 8 to 12 equivalents of hydroxylamine in an anhydrous basic solvent which acts as an acid scavenger for hydroxylamine hydrochloride solvent such as pyridine for a period of time sufficient to provide a recoverable quantity of estriol-16,17-diacetate-6-oxime which is then recovered and dissolved in a polar, protic solvent such as absolute ethanol containing powdered zinc, $NH_4OH$ and $NH_4OA_c$. The reaction mixture is then slowly warmed to reflux temperature for a time sufficient to form the 6α-amino derivative. The 6α-aminoestriol-3,16,17-triacetate can be converted to the triol using NaOH. The 6α-amino estriol triacetate or estriol can serve as precursors for various 6α-substituted compounds. For example, preparation of 6α-(N-diglycolyamido)estriol by treating the 6α-amino compound with diglycolic anhydride provides a product which is particularly useful as a hapten in the aforementioned heterogenous assay when the hapten is labeled with a detectable marker such as a radioisotope, chromophore, fluorofore or, preferably, an enzyme such as alkaline phosphatase, peroxidase or beta galactosidase. Substituting the 6α-amino group with sidechains provides a 6α estriol derivative which exhibits superior sensitivity with respect to antibodies specific for estriol. The 6α-aminoestriol can be derivatized with substituents such as succinic anhydride to form 6α-(succinimidyl)estriol, Bolton Hunter Reagent to form 6α-(N-p-hydroxy-m-iodophenyl-propionamide) estriol, pentazoic anhydride to form 6α-(N-pentanoylamido)estriol and hexanoic anhydride to form 6α-(N-hexanoylamido)estriol and thereby provide useful enzyme conjugate precursors. Other sidechains such as a carbon chain of from about 4 to 14 carbon atoms in length, which may have O, N or S interposed between the carbon atoms, terminated with carboxyl, amino or sulfhydryl which can couple with the enzyme are also suitable. The derivatized 6α-estriols can be conjugated to a carrier protein such as bovine serum albumin, keyhole limpet hemocyanin (KLH) or ovalbumin by preparing N-hydroxysuccinimide esters from the estriol acid and reacting them with the protein's primary amino groups. The resulting protein conjugate is dialyzed to isolate protein from unreacted ester to render it useful as immunogens for antibody development in suitable animals such as rabbits, mice or goats.

EXAMPLE I

Preparation of the 6-α Substituted Estriol Derivatives

Preparation of estriol-3,16,17-triacetate (2):

To estriol (50.0 g, 173.6 mmol) in a 1 L flask at room temperature under argon was added anhydrous pyridine (200.0 mL). After stirring into solution, acetic acid (300.0 mL) was added and the reaction stirred for 24–26 hours at room temperature under argon. Following this, EtOAc (300.0 mL) was added and the solution was concentrated in vacuo to a viscous oil. The oil was dissolved in EtOAc (400.0 mL) and washed successively with 0.5N aq. HCl (250.0 mL), saturated aqueous sodium bicarbonate (300.0 mL), and saturated aqueous sodium chloride (250.0 mL). The organic solution was then dried with $MgSO_4$, filtered and concentrated in vacuo to provide 69.2 g (167 mmol, 96%) of estriol-3,16,17-triacetate.

$^1$H NMR (250 MHz, $CDCl_3$ ppm.): 0.85 (s, 3H), 1.3–2.05 (m, 10 H), 2.05 (s, 3H), 2.1 (s, 3H), 2.26, (S, 3H), 2.32 (M, 1H), 3.85 (m, 2H), 4.99 (d, 1H), 5.19 (dt, 1H), 7.26 (d, 1H), 7.85 (dd, 1H), 7.95 (d, 1H).

$^{13}$CD NMR (250 MHz, $CDCl_3$, ppm.): 12.9 (methyl), 20.97 (methylene), 21.06 (methyl), 21.13 (methyl), 25.6 (methylene), 26.9 (methylene), 29.3 (methylene), 31.9 (methylene), 36.7 (methylene), 37.7 (methine), 43.7 (quat.), 43.8 (methine), 48.1 (methine), 77.97 (methine), 86.0 (methine), 118.6 (CH, arom.), 121.5 (CH, arom.), 126.3 (CH, arom.), 137.4 (quat-arom.), 137.9 (quat-arom.), 148.5 (quat-arom.), 169.7 C=O), 170.8 (C=O).

FAB/MS (GLY/DMF): 429 ($M^+$, BASE), 388, 309, 267, 173.

Preparation of 6-ketoestriol (3):

To estriol-3,16,17-triacetate (69.1 g, 166.7 mmol) in a 1 L flask at room temperature, in the dark and open to the atmosphere, was added acedic acid (200.0 mL) with stirring. A solution of chromium trioxide (50.0 g, 300 mmol) was added acetic acid (200.0 mL) with stirring. A solution of chromium trioxide (50.0 g, 300 mmol) in acedic acid/water (300 mL/60 mL) in a 500 mL addition funnel was added over a period of about one hour. The addition funnel was removed and the reaction stirred at room temperature, in the dark and open to the atmosphere, for an additional 44–48 hours.

The reaction mixture was next poured into 1 L of water and the resulting solution extracted with ethyl ether (3×500 mL) in a 2 L separatory funnel. The organic phases were combined and set aside. An additional 300.0 mL of water was added to the aqueous phase, which was extracted a final time with ethyl ether (400 mL) and combined with the previous ether extracts (~1600 mL total volume). The organic phase was then carefully washed with saturated aqueous sodium bicarbonate (3×300.0 mL) in a 3 L separatory funnel. The combined aqueous bicarbonate phases were back extracted once with ether (125 mL) to provide an ether solution which was added to the main organic solution (~1600 mL).

The organic phase solution was then washed with a mixture of saturated aqueous $NaHCO_3$/1M $Na_2CO_3$ (3/1 v/v, 3×400 mL). The aqueous $NaHCO_3$/1M $Na_2CO_3$ solution was also back-extracted with ether (125 mL) as previously described. Finally, the organic phase solution was washed with 300 mL of water. The ether solution was then dried with granular $MgSO_4$, filtered and concentrated in vacuo with an aluminum foil cover in place to provide about 50 g crude material as a glassy solid. This product was stored overnight in a refrigerator and then purified.

Stock solvent solutions were prepared as follows:

A 6 L stock solution of hexane/EtOAc (6/1, v/v), labeled solvent A; a 6 L stock solution of hexane/EtOAc (4/1, v/v) labeled solvent B; a 2 L stock solution of hexane/EtOAc (3/1, v/v), labeled solvent C; a 6 L stock solution of hexane/EtOAc (2/1, v/v) labeled solvent D. A 2 L volume (1000 g) of 2320–400 mesh silica gel-60 was equilibrated with solvent A and poured into a 8×60 cm chromatography column and 1 L of solvent A was collected by gravity flow. As the 1 L of solvent A solution was collected, the crude product was dissolved into a volume of about 75 mL ethyl ether, adsorbed onto about 80 mL (40 g) silica gel-60 (230–400 mesh) and then carefully concentrated to a free flowing powder. This produce/silica mixture was applied to the top of the column and solvent A (2 L) carefully applied to the column, collected by gravity and discarded.

Solvent B (3 L) was then applied to the top of the column, collected via gravity and discarded. Twelve sequentially numbered fractions (#1–12) eluting with solvent B (200–225 mL each) were then collected via gravity. The eluant was then switched to solvent C and six sequentially numbered fractions (#13–18) eluting with solvent C (200–225 mL each) were collected via gravity. Finally, the eluant was switched to solvent D and twenty seven sequentially number fractions (#19–45) eluting with solvent D (200–225 mL each) were collected via gravity.

The presence of product in the collected fractions was purified by standard TLC techniques using silica gel 60 coated glass plates and elution with hexane/EtOAc (1/1, v/v). The plates were viewed under U.V. light and then visualized by spraying with ceric sulfate solution and heating which developed a purple product spot with an Rf value of about 0.50 from the collected fractions (#20–33). An impurity appeared as a single red spot with an Rf value of about 0.60 in the initial fractions collected (#1–15) recovered estriol-triacetate. Later fractions (#36–45) had a material with a greyish spot having an Rf of about 0.40 which impurity was discarded. The combined product fractions (#20–33) were concentrated in vacuo on a rotary evaporator using EtOAc as needed for transfer solvent as the product was isolated into a 50 mL round bottom flask. After final concentration and drying on high vacuum, 13.24 g (18.5%; 21.8% based on recovered starting material) of 6-ketoestriol-3,16,17-triacetate was obtained.

$^1$H NMR (250 MHz, Acetone-$d_6$, ppm.): 0.95 (s, 3H), 1.55–2.8 (m, 11H), 2.0 (s, 3H), 2.08 (s, 3H), 2.3 (s, 3H), 4.98 (d, 1H), 5.18 (dt, 1H), 7.35 (dd, 1H), 7.55 (D, 1H), 7.65 (d, 1H).

$^{13}$CD NMR (250 MHz, Acetone-$d_6$, ppm.): 13.0 (methyl), 20.8 (methyl), 20.9 (methyl), 20.95 (methyl), 25.6 (methylene), 32.2 (methylene), 37.1 (methylene), 39.7 (methine) 43.2 (methine), 43.3 (methine), 48.6 (methine), 78.3 (methine), 86.5 (methine), 120.3 (CH, arom.), 127.6 (CH, arom.), 127.7 (CH, arom.).

E1-DIP/MS (70-EV): 428 ($M^+$), 386 (BASE), 284, 173.

Preparation of estriol-16,17-diacetate-6-oxime (4)

To 6-ketoestriol-3,16,17-triacetate (8.20 g, 19.14 mmol) at room temperature under argon was added anhydrous pyridine (75.0 mL) with stirring until the steroid dissolved. Hydroxylamine hydrochloride (13.3 g, 191.4 mmol, 10 equiv.) was added in one portion and the flask sealed with new septa under argon. The flask was placed into an oil bath preheated to 60–70° C. (at a depth equal to the volume of the reaction solution in the flask) in the dark and stirred for about 5 hours. The reaction was monitored periodically to ascertain that the temperature did not elevate since hydroxylamine hydrochloride poses an explosion hazard when heated above 115° C.

After stirring for 5 hours, the flask was removed from the oil bath and all residual oil on the flask was removed with solvent, the stir bar was removed and the solution concentrated in vacuo (with a blast shield in place) to a volume of about 20–25 mL with caution being taken not to evaporate to dryness. The residual solution was dissolved into EtOAc (500 mL) and water (150 mL) with stirring for 5 minutes. The water layer was removed and the organic solution extracted twice more with water (2×100 mL). The combined aqueous phases were back extracted once with EtOAc (150 mL) whereupon the combined organic phases were dried with granular $MgSO_4$, filtered and concentrated in vacuo to a volume of about 100 mL. The solution was then transferred to a tarred flask, concentrated in vacuo and dried under high vacuum to provide about 8.0 g (quant.) estriol-16,17-diacetate-6-oxime as a white solid containing trace residual pyridine. The product was purified using standard TLC techniques using silica gel 60 coated glass plates and elution with hexane/EtOAc (1/1, v/v) and had an Rf value of about 0.2 (starting material had an Rf value of about 0.4) when visualized by spraying the plates with ceric sulfate solution and heating.

$^1$H NMR (250 MHz, Acetone-$d_6$, ppm.): 0.9 (s, 3H), 1.4–2.4 (m, 10H), 2.0 (s, 3H), 2.05 (s, 3H), 3.15 (dd, 1H), 4.98 (d, 1H), 5.16 (dt, 1H), 6.81 (dd, 1H), 7.17 (d, 1H), 7.45 (d, 1H).

$^{13}$CD NMR (250 MHz, Acetone-$d_6$, ppm.): 13.1 (methyl), 20.8 (methyl), 20.9 (methyl), 25.9 (methylene), 32.5 (methylene), 37.1 (methylene), 37.5 (methine), 42.2 (methine), 44.3 (quat.), 49.2 (methine), 78.5 (methine), 86.7 (methine), 110.6 (CH, arom.), 117.2 (CH, arom.), 126.6 (CH, arom.), 153.6 (C=O), 156.3 (C=O), 170.7 (C=N).

E1-DIP/MS (70 EV): 386 (M-1), 371 (M-$NH_2$), 311, 269, 251, 157, 115 (BASE).

Preparation of 6α-aminoestriol-16,17-diacetate (5)

To estriol-3,16,17-triacetate-6-oxime (8 g crude, 19.14 mmol theoretical transferred to 150.0 mL of absolute ethanol) in a 2 L round-bottom flask equipped with a stir bar and septa, under argon atmosphere, was added absolute ethanol (600.0 mL) whereupon the solution was stirred until completely dissolved. Next, added sequentially, were zinc dust in one portion (40.0 g) followed by ammonium hydroxide (375 ml) in one portion followed by ammonium acetate (60.0 g) in one portion, all with stirring under argon. The flask was equipped with a cold water condensor and placed into a room temperature oil bath. The bath was warmed slowly from $% to reflux (100° C.) over about an hour while monitoring the reaction carefully to avoid any vigorous exotherm as hydrogen gas evolved. The reaction was then stirred under argon at reflux for about 4.5 hours whereupon the flask was removed from the bath and the solution allowed to cool to about 50° C.

The reaction solution was decanted (in the hood) into another 2 L round bottom flask with rinsing of the first flask with about 50 mL water. The solution was then concentrated in vacuo on a rotary evaporator in a water bath at 50° C. to a volume of about 300 mL. The solution was transferred to a 500 mL flask and further concentrated to about 125 mL whereupon EtOAc (200.0 mL) was added to the flask and the solution reconcentrated to about 125 mL. The flask was stoppered and placed in a refrigerator for about an hour to allow product to precipitate. Precipitated product was then collected by filtration. The resulting cream colored solid was dried on high vacuum at about 40° C. (water bath) for about 0.5 hour to provide 5.4 g of crude material.

To the crude solid was added 40 mL EtOAc with stirring which resulted in a white solid in a yellowish solution. To this was added 20 mL of hexane with stirring for 5 minutes. The resulting white solid product was then collected by vacuum filtration after which an additional 20 mL of hexane was added to the residual filtrate which provided a second crop of white product which was collected by filtration and combined with the first crop of white, solid product. After drying on high vacuum, 5.03 g (13.0 mmol, 68%) 6α-aminoestriol-16,17-diacetate was obtained. The product, purified by standard TLC techniques using silica gel 60 coated glass plates and elution with $CHCl_3/MeOH/NH_4OH$ (90/10/1, v/v), had an Rf value of approximately 0.15 when visualized by spraying the plates with ceric sulfate solution and heating.

$^1$H NMR (250 MHz, Acetone-$d_6$, ppm.): 1.4–2.5 (m, 11H), 1.93 (s, 3H), 2.0 (s, 3H), 4.7 (quart., 1H, 6β), 4.98 (d, 1H), 5.15 (dt, 1H), 6.38 (d, 1H), 6.6 (dd, 1H), 7.08 (d, 1H).

$^{13}$CD NMR (250 MHz, Acetone-$d_6$, ppm.): 12.6 (methyl), 20.2 (methyl), 20.3 (methyl), 25.9 (methylene), 31.9 (methylene), 34.6 (methylene), 36.9 (methylene), 37.3 (methine), 44.2 (methine), 47.9 (methine), 59.5 (C6-methine), 77.9 (methine), 86.1 (methine), 113.6 (CH, arom.), 114.6 (CH, arom.), 126.9 (CH, arom.).

E1-DIP/MS (70 EV): 401 (M$^+$, BASE), 385, 341, 299, 284, 264, 172.

Preparation of 6α-aminoestriol (6)

To 6α-aminoestriol-16,17-diacetate (1.60 g, 4.13 mmol) in a 100 mL round bottom flask was added absolute ethanol (30.0 mL) with stirring under argon at room temperature. A sodium hydroxide solution was prepared as follows:

Solid NaOH (4.0 g) was added to a 25 mL beaker followed by 6.0 g nanopure water with stirring until the NaOH dissolved and then allowing the solution to cool to room temperature. This provided a 40% (w/w) solution of aqueous NaOH. Next, 7.5 mL of this solution was added via a 10.1 mL syringe into the 100.0 mL reaction flask with stirring under argon at room temperature. The reaction was stirred under argon at room temperature for 5.5 hours eventually becoming heterogenous.

2N aqueous HCl (20.0 mL) was then added with the solution becoming homogenous as it stirred. Concentrated HCl (between 4 and 6 mL) was carefully added dropwise via pipette to the stirring aqueous reaction solution until a pH value of about 8 was obtained. The stirring bar was removed and the solution was concentrated on a rotary evaporator under vacuum in a water bath at about 25° C. to remove ethanol just to the point that the solution in the flask became cloudy. To the cloudy reaction solution was added dropwise via pipette 10 to 12 drops of 5N aqueous NaOH with stirring to provide a white/creme precipitate which was collected by filtration.

The collected solid was placed into a 50 mL beaker and 20.0 mL MeOH added. To the 50 mL beaker was added dropwise via pipette with stirring 8 drops of conc. HCl. About 90–95% of the solid dissolved into solution which was filtered through a medium sintered glass funnel to remove undissolved solid into a tarred 25 mL round bottom flask. The solution was then carefully concentrated on a rotary evaporator under vacuum in a water bath at about 25° C. to provide crude product which was dried under high vacuum for about 0.5 hour. The crude product was titrated with 15 mL acetone while stirring, decanted and titrated a second time with 5 mL acetone. After decantation the creme colored solid product was dried under high vacuum for about 0.5 hour to provide 1.2 g (3.96 mmol, 96%) of 6α-aminoestriol. The product, purified by standard TLC techniques using silica gel 60 coated glass plates and elution with $CHCl_3/MeOH/NH_4OH$ (60/40/10, v/v), had an Rf value of about 0.53 when visualized by spraying the plates with iodine solution and allowing it to stand for several minutes.

$^1$H NMR (250 MHz, $CD_3OD$, ppm.): 0.78 (s, 3H), 1.2–2.3 (m, 11H), 3.48 (d, 1h), 4.06 (dt, 1H), 4.52 (quart., 1H, 6β), 6.75 (dd, 1H), 6.85 (d, 1H), 7.22 (d, 1H).

$^{13}$CD NMR (250 MHz, $CD_3OD$ ppm.): 12.7 (methyl), 26.97 (methylene), 34.7 (methylene), 34.8 (methylene), 37.7 (methylene), 38.8 (methine), 44.8 (methine), 48.4 (methine), 51.3 (C6-methine), 78.6 (methine), 96.4 (methine), 114.4 (CH, arom.), 116.7 (CH, arom.), 128.2 (CH, arom.), 133.3 (quant.), 134.7 (quant.), 157.2 (quant.).

FAB/MS (GLY/DMF): 287 (M–$NH_2$), 369, 251, 207, 181, 165, 115 (BASE).

Preparation of 6α-(N-diglycolylamido)estriol (7)

To 6α-aminoestriol (700 mg, 2.31 mmol) in a 25 mL flask, under argon at room temperature, was added anhydrous DMF (10.5 mL) using a 25.0 mL argon flushed syringe. Diglycolic anhydride (348 mg, 3.0 mmol, 1.3 equiv.) was added in one portion with stirring, followed by TEA (97 μL, 0.694 mmol, 0.30 equiv.) in one portion via a 100 μL syringe. The reaction was stirred under argon at RT for about 3 hours whereupon the stir bar was removed and the reaction concentrated in vacuo to dryness under high vacuum to provide crude product.

Stock solvent solutions were prepared as follows: a 2.1 L solution of $CHCl_3/MeOH/NH_4OH$ (60/40/5) labeled solvent A; a 1.1 L solution of $CHCl_3/MeOH/NH_4OH$ (60/40/10) labeled solvent B. A 300 mL volume (150 g) quantity of 70–230 mesh silica gel-60 was equilibrated with solvent A and poured into a 4×50 cm chromatography column and 250 mL of solvent A was collected by gravity flow. As the 250 mL of solvent A solution was collected, the crude product was dissolved into a volume of about 200 μL $CHCl_3$/MeOH (4/1) with swirling and then adsorbed onto about 2 mL (1 g) silica gel-60 (70–230 mesh) and stirred to a free flowing powder. This product/silica mixture was applied to the top of the column and solvent A (225 mL) carefully applied to the column, collected by gravity and discarded.

Forty sequentially numbered test tube fractions (#1–40) eluted with solvent A (11–12 mL each) were then collected via gravity. The eluent was then switched to solvent B and sixty sequentially numbered fractions (#41–100) eluted with solvent B (11–12 mL each) were collected via gravity. The solvent flow from the column was then stopped.

The presence of product in the collected fractions was verified by standard TLC techniques using silica gel 60 coated glass plates and elution with CHCl₃/MeOH/NH₄OH (60/40/10). The plates were viewed under U.V. light and then visualized by spraying with ceric sulfate solution which developed a product spot with an Rf value of about 0.47 from the collected fractions (#38–84). A minor impurity appeared coincidentally as a shadow spot just above the product in all of these fractions. The combined product fractions (#38–84) were concentrated in vacuo on a rotary evaporator at no more than 35° C. since excessive heat could cause the sidechain in the product to irreversibly cyclize onto itself. Methanol was used as needed for transfer solvent as the product was isolated into a tarred 25 mL round bottom flask. After final concentration and drying on high vacuum (1 hour), 600 to 700 g of crude white solid product was obtained.

Recrystallization: The crude product was dissolved into 20.0 mL of methanol with stirring, placed onto a rotary evaporator and carefully concentrated until the solution started to turn milky as product just began to precipitate (about 5 mL solution in the flask). Product was collected by filtration through a medium 2 mL sintered glass funnel rinsing with 2×1 mL additional MeOH. The product was removed from the sintered glass funnel using a spatula and transferred to a tarred 10 mL 14/20 round bottom flask.

The filtrate was placed back into a round bottom flask and reconcentrated to about 4 mL. Hexane (0.5 mL) was added to the solution, resulting in a second crop of product which was collected through the sintered glass funnel as previously described. The combined product was transferred to the tarred 10 mL flask as above and then carefully dried on high vacuum for about 1 hour to provide 454 mg (1.1 mmol, 48%) of 6α-(N-diglycolylamido)estriol. Purity by HPLC was found to be 98.5%

¹H NMR (250 MHz, CD₃OD, ppm.): 0.78 (s, 3H), 1.3.–2.4 (m, 11H), 3.45 (d, 1h), 3.95 (s, 2H), 4.05 (m, 1H), 4.08 (s, 2H), 5.19 (quart., 1H), 7.6 (dd, 1H), 7.65 (d, 1H), 7.13 (d, 1H).

¹³CD NMR (250 MHz, CD₃OD ppm.): 13.1 (methyl), 27.4 (methylene), 35.1 (methylene), 36.1 (methylene), 38.2 (methylene), 39.4 (methine), 45.7 (methine), 71.54 (methylene), 72.2 (methylene), 78.8 (methine), 90.8 (methine), 115 (CH, arom.), 115.6 (CH, arom.), 127.6 (CH, arom.).

FAB/MS (GLY/DMF): 419 (M⁺), 359, 287, 270, 237, 197, 157, 115 (BASE).

Preparation of 6α-(N-diglycolylamido)estriol-NHS-ester (8)

6α-(N-diglycolylamido)estriol (10.0 mg, 0.0239 mmol) was added to a 1 dram amber vial and placed under argon at room temperature. Anhydrous DMF (1000.0 μL) was added to the vial using a 1000 μL argon flushed micro-syringe followed by the addition of dicyclohexylcarbodiimide (DCC) (5.42 mg, 0.00263 mmol, 1.1 equiv.) in one portion with stirring. After 5 minutes, N-hydroxysuccinimide (NHS) (3.0 mg, 0.0263 mmol, 1.1 equiv.) was added and the reaction was stirred under argon for about 24 hours after sealing the vial under argon with parafilm.

After the mixture had stirred for about 24 hours, the reaction solution was quickly and carefully filtered into a new 1 dram amber vial through a, small cotton plug fitted into a disposable glass pipette using a pipette bulb to aid filtration. Product verification was performed by standard TLC techniques using silica gel 60 coated glass plates and elution with CHCl₃/MeOH/NH₄OH (60/40/10, v/v/v). The plates were visualized by spraying with iodine solution which developed a product spot with an Rf value of about 0.59 (the starting material developed a spot with an Rf value of about 0.31). The vial was sealed with a new septum, purged with argon for about 5 minutes and then sealed with parafilm. The maximum theoretical yield was then calculated for the in situ generated solution. Maximum theoretical yield: (0.00239 mmol)×(516)/1.0 mL)=12.33 mg/mL 6α-(N-diglycolylamido)estriol-NHS-ester (not shown in Scheme I) which is capable of coupling directly to an enzyme such as ALP to provide a labeled hapten for use in the estriol assay.

Synthesis of 6α-(N-diglylcolylamido)estriol

Scheme I

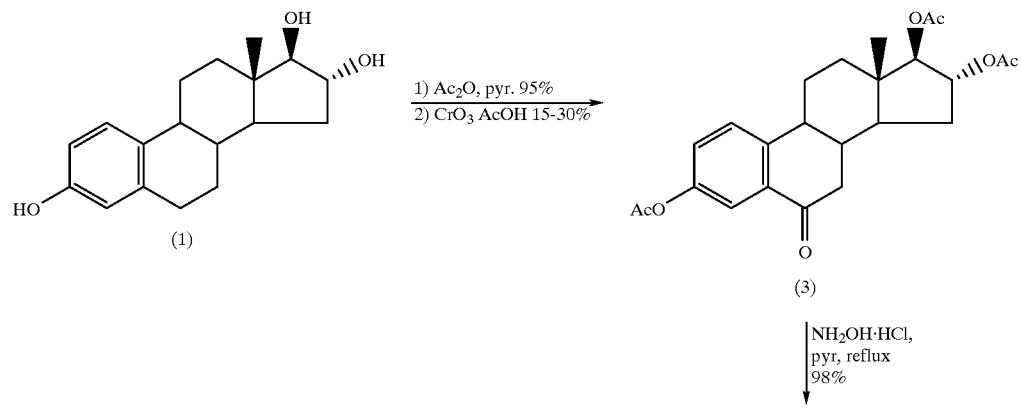

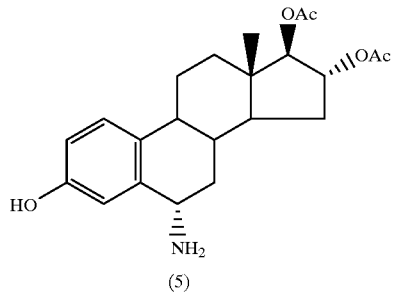

(5)

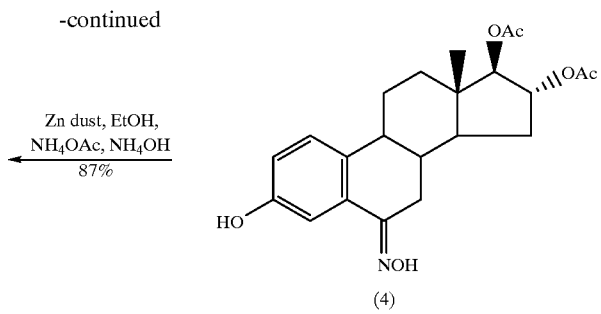

(4)

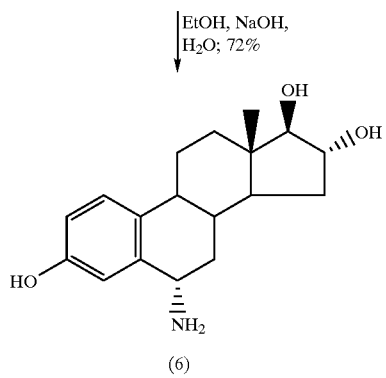

(6)

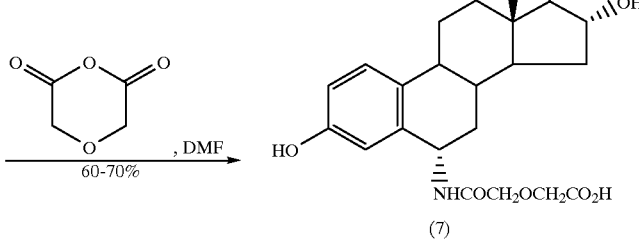

(7)

EXAMPLE II

Preparation of 6-α Estriol-KLH Conjugates and Their Use in Generating Antibodies Keyhole limpet hemocyanin (KLH) was dissolved in bicarbonate buffer pH=8.5. The NHS ester (compound 8) and protein were reacted at a 500:1 hapten to protein ratio for 4 hours at room temperature and the resulting protein conjugate was dialyzed to isolate protein from unreacted ester. The resulting KLH conjugate was emulsified in complete Freunds adjuvant and used to immunize rabbits with 0.25 mg injections.

EXAMPLE III

Preparation of 6-α Estriol-ALP Conjugates

Alkaline phosphatase was exchanged into bicarbonate buffer pH=8.5. The NHS ester and protein were reacted at a 5:1 hapten to protein ratio for 2 hours at room temperature and the protein conjugate was dialyzed to isolate protein from unreacted ester.

EXAMPLE IV

Determination of Estriol in Serum Using Various Estriol-ALP Conjugates

The 6α-estriol-ALP conjugate prepared as described in Example III and 3 other ALP conjugates of estriol haptens [estriol-7-carboxyethylthioester, estriol-3-carboxyethylester and estriol-6-carboxymethylester (CMO)] were analyzed in a Bayer Immuno 1™ analyzer (Bayer Diagnostics).

This assay is a competitive magnetic separation immunoassay using the following materials: i) a monoclonal antibody to fluorescein isothiocynate which has been immobilized on magnetic particles, ii) a polyclonal rabbit antibody against human estriol prepared as described in Example II which has been purified and labeled with fluorescein isothiocyanate and iii) estriol derivatized alkaline phosphatase. The polyclonal rabbit antibody against human estriol is bound to the magnetic particles via the fluorescein isothiocynate tag on the antibody and the anti-fluorescein isothiocynate on the magnetic particles. Estriol in human serum competes with the conjugated estriol-ALP for binding to the immobilized anti-estriol antibody. The magnetic particles are washed and the ALP substrate (para nitrophenyl phosphate) added. The rate of hydrolysis of the substrate is measured by absorbance at 405 nm and expressed as milli absorbance per minute (mA/min) units which results are then converted to ng/mL.

Data generated using serum samples containing 0, 0.15, 0.5, 2, 10 and 30 ng/ml estriol tested in this manner using each of the four haptens presented in Table 1. The sensitivity of an immunoassay is measured by the amount of separation between the low level calibrators. As demonstrated in Table 1, the 6α-diglycolylamido-estriol hapten conjugate produces an immunoassay which is approximately two times more sensitive than the other hapten conjugates.

TABLE 1

| [Estriol] | 6-α-diglycol-amido-Estriol | Estriol-7-carboxy-ethylthio ester | Estriol-3-carboxy-methyl ester | Estriol-6-CMO |
|---|---|---|---|---|
| 0 | 451 | 210 | 312 | 321 |
| 0.15 | 395 | 196 | 302 | 287 |
| 0.5 | 325 | 184 | 284 | 245 |

TABLE 1-continued

| [Estriol] | 6-α-diglycol-amido-Estriol | Estriol-7-carboxy-ethylthio ester | Estriol-3-carboxy-methyl ester | Estriol-6-CMO |
|---|---|---|---|---|
| 2 | 229 | 160 | 265 | 215 |
| 10 | 138 | 141 | 241 | 165 |
| 30 | 74 | 115 | 221 | 119 |
| Sensitivity | 56 | 14 | 10 | 34 |

We claim:

1. 6α-aminoestriol-16,17-diacetate.
2. A method for the preparation of 6α-aminoestriol-16,17-diacetate which comprises the steps of:

a) reacting 6-ketoestriol-3,16,17-triacetate with about 8 to 12 equivalents of hydroxylamine.HCl at an elevated temperature in pyridine for a period of time to provide a recoverable quantity of estriol-16,17-diacetate-6-oxime;

b) recovering the estrio-16,17-diacetate-6-oxime and dissolving it in absolute ethanol along with powdered zinc and adding $NH_4OH$ followed by $NH_4OAc$; and c) warming the reaction mixture slowly to reflux temperature and holding the reaction mixture at reflux temperature for a time sufficient to form the desired product.

3. 6α-(N-diglycolylamido)estriol.
4. 6α-aminoestriol.
5. 6α-(N-diglycoylamido)estriol NHS-ester.

* * * * *